United States Patent
Hopper (10) Patent No.: US 6,543,445 B1
(45) Date of Patent: Apr. 8, 2003

(54) NON-INVASIVE SINUS PAIN RELIEVING ASSEMBLY AND METHOD

(76) Inventor: William J. Hopper, 16 River Bend Rd., White Salmon, WA (US) 98672

( * ) Notice: Subject to any disclaimer, the term of this patent is extended or adjusted under 35 U.S.C. 154(b) by 0 days.

(21) Appl. No.: 09/664,191

(22) Filed: Sep. 18, 2000

Related U.S. Application Data (63) Continuation of application No. 09/028,873, filed on Feb. 22, 1998, now Pat. No. 6,182,660.

(51) Int. Cl.$^7$ ................................................. A62B 9/00
(52) U.S. Cl. ............... 128/200.24; 128/898; 128/207.13
(58) Field of Search ........................ 128/203.21, 204.28, 128/204.18, 205.75, 207.13, 200.22, 200.24, 201.23, 201.24, 203.28, 205.13, 205.16, 205.17, 206.12, 206.21, 206.24, 206.28, 898; 604/36, 94; 606/201, 191, 196, 1

(56) References Cited

U.S. PATENT DOCUMENTS

| | | | |
|---|---|---|---|
| 743,294 A | | 11/1903 | Knowles |
| 958,569 A | * | 5/1910 | Venner .................. 128/207.13 |
| 2,428,451 A | | 10/1947 | Emerson |
| 2,485,184 A | | 10/1949 | Blackman et al. |
| 2,737,177 A | | 3/1956 | Anklin |
| 3,667,463 A | | 6/1972 | Barnes |
| 4,403,611 A | | 9/1983 | Babbitt et al. |
| 4,498,472 A | | 2/1985 | Tanaka |
| 4,817,626 A | | 4/1989 | Blaine |
| 4,934,359 A | | 6/1990 | Blaine |
| 4,995,386 A | | 2/1991 | Ng |
| 5,024,612 A | | 6/1991 | Honert et al. |
| 5,024,653 A | | 6/1991 | Kohnke |
| 5,062,835 A | | 11/1991 | Maitz et al. |
| 5,098,386 A | | 3/1992 | Smith |
| 5,114,415 A | | 5/1992 | Shedlock |
| 5,318,548 A | | 6/1994 | Filshie |
| 5,431,636 A | | 7/1995 | Stangerup |
| 5,527,275 A | | 6/1996 | Ginsberg |
| 5,596,983 A | * | 1/1997 | Zander et al. ......... 128/204.18 |
| 5,599,332 A | | 2/1997 | Cashel |
| 6,182,660 B1 | * | 2/2001 | Hopper ................... 128/207.13 |

* cited by examiner

Primary Examiner—Glenn K. Dawson
(74) Attorney, Agent, or Firm—Malloy & Malloy, P.A.

(57) ABSTRACT

A non-invasive device and attendant method specifically designed to regulate and effectively equalize the pressure between the sinus cavities and middle ear, and the nasal cavity and nasopharynx. The relieving of the pressure within the sinus cavities in turn relieves pain normally associated with such a condition. The pressure equalizing assembly and method comprises establishing a seal about the nose and nostrils of the user and thereby effectively isolating the nasal cavity and nasopharynx, when the user swallows, and further establishing direct fluid communication with a vacuum chamber and a pressure regulating assembly so as to create an initial negative pressure within the nasal cavity and nasopharynx. Fluid in the form of mucous, liquid and/or air is thereby forced from the sinus cavities, which may define a zone of relative high pressure such that the pressure is effectively regulated between the sinus cavities, middle ear, nasal cavities and nasopharynx through the selective manipulation of the pressure regulating assembly thereby providing immediate relief from sinus pain while helping to relieve middle ear pressure and associated symptoms.

29 Claims, 7 Drawing Sheets

NON-INVASIVE SINUS PAIN RELIEVING ASSEMBLY AND METHOD

CLAIM OF PRIORITY

This is a continuation application of presently pending U.S. patent application Ser. No. 09/028,873, which was filed on Feb. 22, 1998, now U.S. Pat. No. 6,182,660.

BACKGROUND OF THE INVENTION

1. Field of the Invention

This invention relates to a non-invasive sinus pain relieving assembly and an attendant method for equalizing the pressure between the sinus cavities and the middle ear by isolating the nasal cavities and nasopharynx and subjecting this area to a negative pressure thereby providing immediate relief of normally involved sinus pain, and helping to release trapped middle ear pressure.

2. Description of the Related Art

Currently, there is no commercially available, portable product or device available to the general public without a prescription that mechanically but non-intrusively relieves sinus and middle ear pressure. Present methods of treatment of sinus pain are often chemically related such as numerous vasoconstricting local agents or prescription drugs. Indeed, chemical dependency due to the large numbers of vasoconstrictors in use is very wide spread. In addition, tissue damage from the improper and excessive use of these vasoconstricting chemicals may lead to corrective surgery that is sometimes followed by required cosmetic surgery. Of course, surgery in the sinuses and nasal cavity can easily lead to the spread of infectious agents not only to the sensitive membranes involved but also to the bones forming these cavities.

Specifically, each sinus cavity is lined with a mucous membrane which are substantially continuous with the mucous membrane of the nose and throat. When the nose and nasal cavity fail to produce enough mucous, the sinuses are triggered to overcompensate and make up the difference. Normally, the mucous from the sinuses drain into the nasal cavity through small apertures connecting the two areas. However, if the mucous membrane of the sinuses swells or mucous thickens, due to improper hydration, drainage may be impeded. If this happens, pressure inside the sinus cavities may be trapped. This could cause a differential pressure to exist, squeezing sensitive nerves and possibly causing severe headaches or toothaches. This condition is called barotrauma. Furthermore, if outside barometric pressure increases because of normal weather movement, or with a change in altitude, as in a descending aircraft, auto or during recreation, the condition will worsen. The same condition may effect the middle ears if the bony cartilages of the eustachian tubes becomes obstructed with fluids restricting the equalizing of pressure in the middle ear, additionally referred to as aero otitis media.

When these conditions are encountered the sinuses and/or middle ear are subject to the above from numerous sources. The increasing outside pressure communicating with the nasal cavity, and nasopharynx will try to push into the now trapped low pressure sinus or middle ear through its normal drain apertures, reversing the flow of mucous. Upon this occurring, pressure cannot now be effectively equalized by fluid transfer from a sinus and/or middle ear zone of low pressure, to the nasal cavity and nasopharynx zone of high pressure. As is well accepted, fluid will have a tendency to move from a zone of high pressure to a zone of low pressure.

The slight increase in ambient pressure on the body causes a greater pressure differential between the blood in the swollen sinus tissues and the trapped lower pressure inside the sinus cavity. Additional swelling will therefore occur in the sinus tissue. In the middle ear the tympanic membrane or ear drum is pushed in by the higher outside pressure. This pressure differential will also cause an increase in blood flow to and distortion of the inner ear. Sensitive nerves in this inner ear area will be effected leading to possible pain and/or temporary hearing impairment or both. Of course the actual effects to the human body will vary depending on the size of the pressure differential as set forth above and the duration that such pressure differential is allowed to continue. However, the stress on these delicate membranes opens the door for bacterial infection that can lead to numerous well recognized complications.

Accordingly, there is a need for a mechanically operable, non-intrusive device and attendant method that allows for the rapid release of trapped pressure in the sinus cavities and middle ear thereby serving to equalize the pressure in these zones by taking advantage of the physiological fact that all paranasal sinuses open into the lateral wall of the nasal cavity by means of small apertures to allow for the normal passage or drainage of mucous and accordingly sinus pressure. The middle ear similarly communicates with the nasopharynx by means of the eustachian tube, to drain fluids and maintain a pressure balance with the nasopharynx. A preferred mechanically operable device and method to accomplish the equalization of pressure will isolate the nasal cavity from ambient pressure conditions and establish fluid communication between the rapid acting and easily manipulated pressure regulating structure which will serve to reduce the pressure in the nasal cavity and the nasopharynx thereby forcing the transfer of fluid from the now high pressure zones of the sinus cavities and/or middle ear causing the desired equalization of pressure.

SUMMARY OF THE PRESENT INVENTION

The present invention relates to a portable, non-invasive sinus pain relief assembly and method for the relief of sinus pain through the equalization of pressures between the sinus cavities and the nasal cavity and/or nasopharynx. Common to at least some of the preferred embodiments of the structure of the present invention, to be described in greater detail hereinafter, is the utilization of a mask having a body portion with a hollow interior and a continuous seal structure extending about the outer periphery of the mask. The seal is specifically structured and disposed to define sealing engagement with the face of the user in a surrounding area about the nose and nostrils of the user, and in somewhat outwardly spaced relation thereto, so as to avoid any type of intrusive penetration of the nasal cavity through the nostrils. By establishing the surrounding seal of the present invention, the nasal cavity and associated nasopharynx are isolated from ambient pressure, particularly when the uvula end of the soft palate is forced to rotate rearwardly into engagement with the back portion of the nasopharynx to create a separate pressure chamber of the nasopharynx and nasal cavity. Movement of the uvula in the manner described is accomplished by the patient swallowing while the face mask is in sealing engagement in the aforementioned operative position.

The present invention further comprises a pressure regulating assembly including a vacuum chamber selectively positionable between a collapsed position and an expanded position. The vacuum chamber is connected in preferably direct fluid communication to the inner end of the body portion of the face mask and accordingly in direct fluid communication with the interior of the nasal cavity and nasopharynx, when the aforementioned seal of the mask is disposed in sealing engagement surrounding and effectively isolating the nasal cavity. The pressure regulating assembly is further structured to be selectively manipulated by the hands of the user so as to cause positioning of the vacuum chamber, and parts associated therewith, between the aforementioned collapsed position and expanded position. When in the collapsed position, a minimal amount of air is present within the vacuum chamber. To the contrary, when in the expanded position, the interior volume of the vacuum chamber increases forcing a flow of air from the interior of the mask, and as a result from the interior of the nasal cavity into and/or towards the interior of the vacuum chamber. The result is an initial creation of a negative pressure within the nasal cavity and nasopharynx when the soft palate is forced into engagement with a back portion of the nasopharynx to isolate such cavities. Due to the natural phenomenon of the tendency of fluid to travel from a zone of high pressure towards a zone of low pressure, the initial creation of negative pressure within the nasal cavity will force fluid flow mucous and air through the passages normally interconnecting the sinus cavities with the nasal cavity. Similar fluid flow will result between the cavities of the middle ears and the nasopharynx. The result of course will be an equalization of pressure and the immediate relief of pain caused by swelling and the existence of high pressure in the aforementioned middle ear and/or sinus cavities.

In accomplishing the above results, the present invention contemplates a first structural embodiment, wherein the pressure regulating assembly comprises a flexible material bellows having a hollow interior and is positionable between the aforementioned outwardly expanded position and inwardly collapsed position. The inherent flexibility from which the bellow is formed serves to normally bias the bellows into the outwardly expanded position. An inwardly directed force or pressure exerted on the outer end of the bellows will cause its positioning into the collapsed position. This will vacate the majority of air within the vacuum chamber which is defined by and within the hollow interior of the bellows. The bellows has its inner or proximal end connected in direct fluid communication with the hollow interior of the mask and accordingly in direct fluid communication with the nasal cavity when the aforementioned peripheral seal on the mask is in sealing engagement and in surrounding relation to the nose and nostrils of the patient. As such, a release of the bellows by the user automatically forces the bellows into the outwardly expanded position due to the inherent flexibility of the bellows as set forth above. This in turn will cause a flow of air from the sealed interior of the mask and accordingly from the nasal cavity itself into the vacuum chamber on the interior of the bellows. An initial negative pressure will result in the interior of the nasal cavity causing any fluid (mucous, liquid and/or air) to flow from the now high pressure zone of the sinus cavities and middle ears into the now low pressure zone of the nasal cavity and nasopharynx through connecting passages and apertures. The pressure in the sinus cavities and/or middle ears will therefore be effectively equalized with the pressure in the nasal cavity and nasopharynx resulting in a relief of any pain caused by the existing increased pressure in the sinus cavities and middle ears.

Yet another preferred embodiment of the present invention is defined by a somewhat similar structure as the above noted first embodiment but differs therefrom by incorporating a housing to substantially surround the bellows and allow its movement between the aforementioned expanded position and collapsed position. Further, a positioning member is attached to the outer or distal end of the bellows and is contacted or engaged by the user when a force is desired to be applied to the bellows to move it from its outwardly expanded position to its inwardly collapsed position.

The housing further includes a lock assembly mounted at least partly thereon and partly on the positioning member, such that cooperative components of the subject lock assembly serve to removably retain the bellows in its collapsed position when the components of the lock assembly are engaged with one another. Accordingly, the bellows, through manipulation of the positioning member, may be selectively moved into its collapsed position prior to the face mask being disposed in sealed engagement about the nose and nostrils of the user. Once the bellows is retained in its collapsed position by interaction of the components of the lock assembly, the face mask may be sealed in the desired and intended position. When the seal is accomplished, a release assembly may be activated which serves to separate or disengage the components of the lock assembly causing the bellows to automatically move into its outwardly expanded position without further manipulation by the hands of the user. The aforementioned negative pressure is initially formed in the nasal cavity, as described above with reference to the other preferred embodiment of the present invention.

Yet another preferred embodiment of the structure of the present invention comprises the pressure regulating assembly being defined by a piston movably mounted within a housing, wherein the interior of the housing defines the vacuum chamber. As with the above described preferred embodiments, the piston is movable between an outwardly extending, expanded position and an inwardly disposed, collapsed position. The piston is normally biased to its outwardly expanded position by the existence of a biasing spring located within the vacuum chamber and positioned and structured to accomplish such biasing. A positioning member is movably connected to the piston and is structured to move along a specific path or track formed in the housing and when so moving force the piston from the outwardly expanded position to the inwardly collapsed position. Additional structural features of the positioning member and housing relative to the travel of the piston include an automatic release of the piston once the positioning member reaches an effective bottom of its inwardly directed stroke. When such occurs the piston is automatically released from its collapsed position towards and into its outwardly expanded position to accomplish the aforementioned initial negative pressure within the nasal cavity. A positioning member is then disposed in its outermost, extended position to again assume its engagement with the piston for repeated positioning of the piston into its collapsed position. Travel of the piston between the collapsed and expanded positions should occur when the face mask has established its sealing engagement about the nose and nostrils of the face of the user. A vent assembly is formed on the body and is associated with a valve structure specifically configured to allow the venting of air from the vacuum chamber as the piston travels from the outwardly expanded position to the collapsed position. The vacuum chamber is of course connected in direct fluid communication with the interior of the body of the mask so as to cause the flow of air from the nasal cavity, through the hollow interior of the mask into the vacuum chamber, thereby defining the formation of the initial negative pressure with the nasal cavity.

The factors set forth above which create pain within the sinus cavities can easily be compounded due to a lack of proper hydration in the nasal cavity and other affected areas. Accordingly, the present invention further contemplates an additional preferred structural embodiment and method including an attachment to the other structural components indicated above that allows steam or heated water vapor or saline solution to "pre-humidify" the nasal cavity and nasopharynx under ambient conditions, prior to instigating the use of the structure and as a part of the method of the present invention to affect a lower pressure in the sinus cavities and middle ear. More specifically, a hydrator assembly comprises a housing having a hollow interior in which heated water or saline solution is placed in order to accomplish the hydration process. The upper end of the hydrator housing includes an opening and surrounding fitting which is adaptable for sealing engagement with the interior of the face mask so as to establish direct fluid communication with the interior of the hydrator housing and the interior of the face mask body. A hand manipulated valve structure is mounted on the hydrator housing and serves to selectively segregate or establish communication between the interior of the hydrator housing and the interior of the mask. In operation, the heated water vapor or steam from the heated water in the interior of the hydrator housing rises upwardly through the opening of the top of the housing when the aforementioned valve structure is in its open position. The water vapor passes into the interior of the mask and eventually into the nasal cavity and nasopharynx. The above set forth "pre-hydration" process occurs when the face mask is sealed about the nose and nostrils of the user and the pressure regulating assembly is disposed in its collapsed position.

It is an object of the present invention to provide a non-invasive sinus pain relief assembly which is compact and portable, and an attendant method which is highly effective in addressing a primary source of common sinus pain.

A further object of the present invention is to provide a sinus pain relief assembly and method which does not require any chemical components in order to relieve sinus pain.

An added object of the present invention is to provide a sinus pain relief assembly which is structured to be maintained in an operative, collapsed position upon engagement with a user's face so as to prevent the introduction of air into the nasal passages upon the operation of the assembly.

Also an object of the present invention is to provide a sinus pain relief assembly and method which is highly effective, yet which operates in a non-invasive manner.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
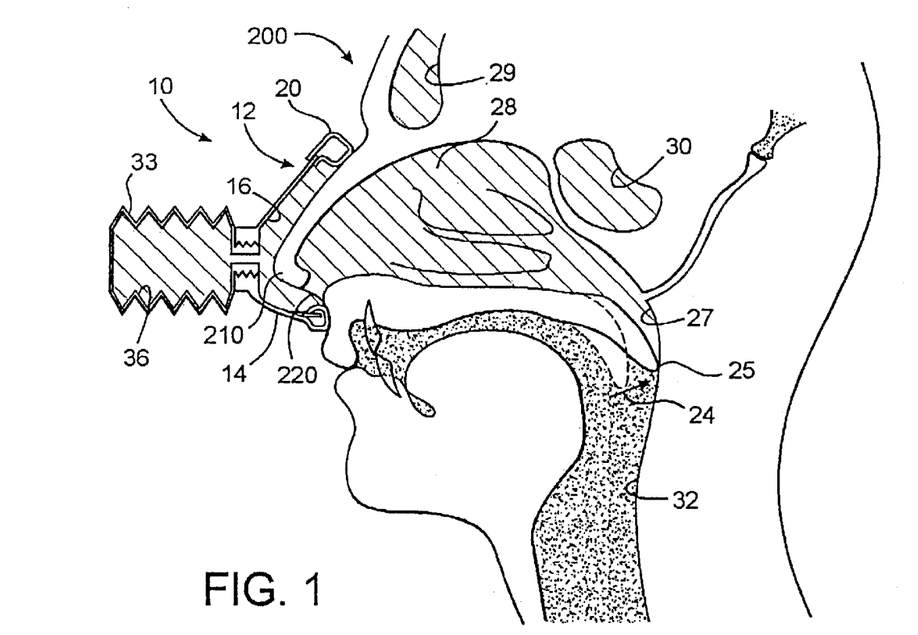
FIG. 1 is a schematic view in partial section indicating the nasal cavity, nasopharynx and sinus cavity and their effective pressurization during operation of the subject invention.
Figure 2:
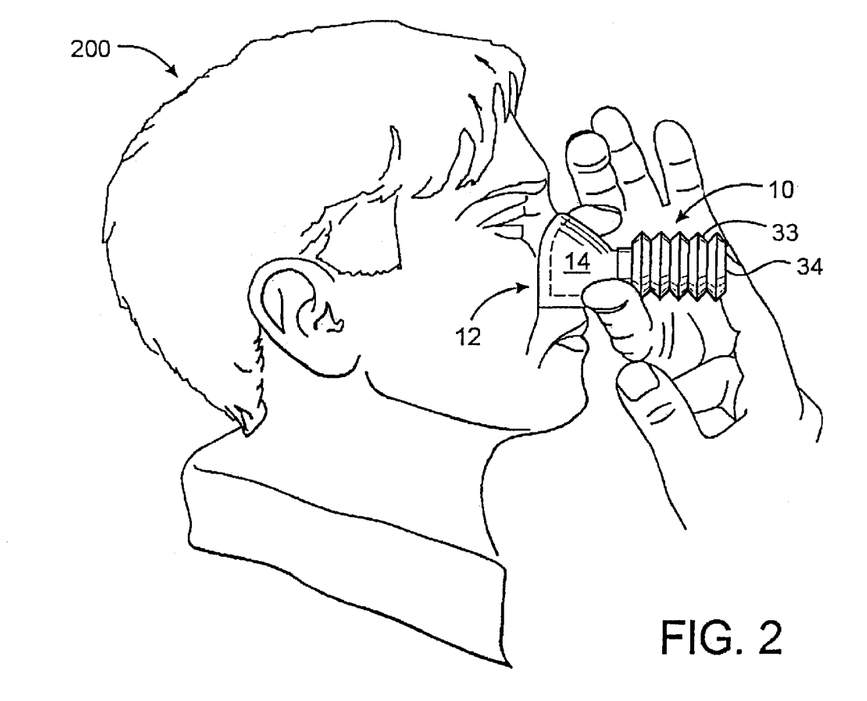
FIG. 2 is a side view in partial perspective showing one preferred embodiment of the present invention in an operative position on a user.

The present invention is directed towards a non-invasive sinus pain relief assembly having one preferred embodiment thereof generally indicated as 10 and shown in an operative position in FIGS. 1 and 2. More specifically, with reference to FIG. 1 the various effective cavities of the patient or user of the subject assembly 10 are delineated for purposes of explanation. The assembly 10 includes a preferably small, mask, generally indicated as 12, having a body portion 14 with a hollow interior as at 16. The outer end of the body portion 14 includes a continuous peripheral seal as at 20 designed to create a seal on the face of the user 200. More specifically, a fluid seal is created in surrounding relation to the nose 210 and in outwardly spaced relation to the nostrils 220. An important feature of the present invention is the structuring of the preferred embodiments herein so as to be non-invasive in that the method of the present invention and the operation of the subject assembly 10, as well as the other preferred embodiments is practiced without entering the nasal cavity per se, through the nostrils 220. Moreover, while any preferably resilient material seal 20 can be employed to achieve mating, generally air-tight engagement with the face and nose of a user, in one preferred embodiment the seal 20 is formed from a self forming material such as hydro-plastic. Specifically, the entire mask 12 or merely the seal portion thereof can be formed of this self forming material, such that a user can conform the seal 20 to the contours of their face, and can achieve a more fluid impervious engagement. Typically, such a forming or molding can be achieved either by placing the mask 12 on the users face, or with some materials, by heating or otherwise treating the material to permit the forming. Such an embodiment is particularly suited when the device is to be used by many individuals, with each individual having there own detachable mask 12.

Again with reference to FIG. 1 the directional arrow as at 24 serves to indicate the rearward rotation of the uvula 25 located at the end of the soft palate into engaging and somewhat sealing relation to the back of the nasopharynx generally as at 27. Further, the nasal cavity 28, as well as the indicated sinus cavities 29 and 30 are effectively isolated from the lower part of the esophagus 32 and from exterior ambient pressures through the mouth and oral cavity and also through the nostril 220. This isolation occurs due to the rearward rotation of the uvula into engagement with the back of the nasopharynx as at 25 and 27 and also the existence of the sealing engagement of the peripheral seal 20 in surrounding and space relation to the nose and nostrils 210 and 220 of the user 200.

Figure 3:
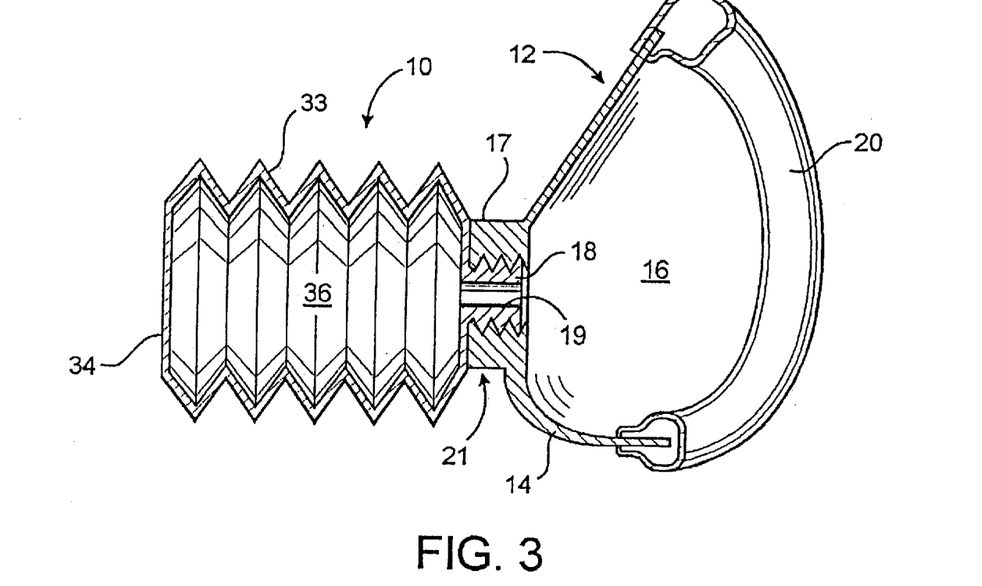
FIG. 3 is a sectional view of the assembled components of the embodiment of FIG. 2.

As will be explained in greater detail hereinafter, the sinus pain relief assembly in the embodiments of FIGS. 1–4 includes a pressure regulating assembly in the form of bellows 33. The bellows 33 are formed from a flexible plastic or like material which is inherently biased to assume the outwardly expanded position as shown in FIGS. 1, 2 and 3, and may include a resilient material bulb or a piston structure. A preferably threaded connector structure as at 35 serves to removably connect the inner or proximal end of the bellows 33 at the inner end of the body portion 14 and in direct fluid communication with the hollow interior 16 of the body portion 14 of mask 12.

The placing of an inwardly directed pressure by the user 200, such as by utilizing their finger, (See FIG. 2) on the outer or distal end 34 of the bellows 33 will cause it to move from the outer, expanded position, where a maximum amount of air is contained within the vacuum chamber 36 defined within the interior of the bellows 33, to an inwardly directed collapsed position, wherein a minimal amount of air is contained within the vacuum chamber 36. Preferably, this collapsed position is achieved before the assembly 10 is sealed against the user's face. When, however, the vacuum chamber 36 is positioned in its collapsed position and once the seal 20 is in sealing engagement about the nose and nostrils of the user 100, the patient facilitates isolation of the lower esophagus 32 by swallowing. Swallowing causes the rearward rotation, in accordance with the directional arrow 24, of the end of the soft palate 25 into engagement with the nasopharynx 27. Indeed, once sealed against a user so as to enclose the nose, there is a low pressure state inside the nasal cavity and nasopharynx, and there is insufficient air movement to move liquids into the assembly 10. As the bellows moves to the expanded position shown in FIGS. 1 and 3, a flow of air, which was under negative tension, will be caused to travel from the interior of the nasal cavity 28 into the hollow interior 16 of the body portion 14 and eventually into the interior of the vacuum chamber 36 of bellows 33. This will initially cause a negative pressure within the nasal cavity 28 and nasopharynx 27. Due to normally existing passages and apertures existing between the sinus cavities 29 and 30 and the nasal cavity 28, the initial negative pressure within the nasal cavity 28 will cause a flow of fluid (mucous, liquid, air) from what may be a now existing high pressure zone in the sinus cavities 29 and 30 into the now low pressure zone of the nasal cavity 28 through the aforementioned interconnecting passages and apertures. The pressure will thereby be equalized between the nasal cavity 28 and the sinus cavities 29 and 30. For purposes of disclosure, certain linear cross hatching existing in FIG. 1 represents the initial negative pressure being exerted on the nasal cavity 28 and effectively on the sinus cavities 29 and 30 as the vacuum chamber 36 and bellows expand from its collapsed position to the pictured, expanded position shown in FIGS. 1 and 3. After use by an individual, the assembly 10 can be removed from its operative position by simply swallowing when it is under a negative pressure state.

Figure 4:
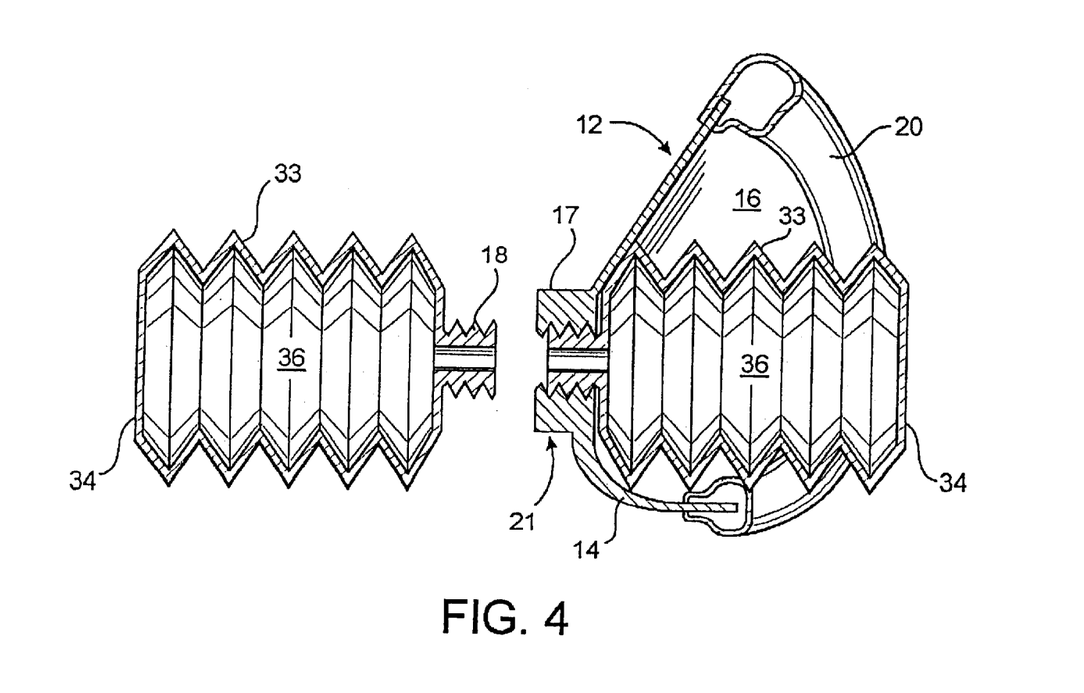
FIG. 4 is a sectional view in detached and exploded form of the embodiment of FIG. 2.

With reference to FIGS. 3 and 4, the preferred embodiment of the present invention further comprises a connector 21, preferably defined by a female, internally threaded collar 17 integrally formed on one end of the body portion 14 and specifically structured to be removably connected to an externally threaded male member 18 preferably integrally formed on the inner or proximal end of the bellows 33. A passage as at 19 is formed within the male member 18 so as to establish direct fluid communication between the hollow interior 16 of the body portion 14 and the vacuum chamber 36 defined on the interior of the bellows 33.

With reference to FIG. 4, the connector 21 is preferably removably connected so as to allow detachment of the male member 18 from the female collar 17 and from its operative position into a stored position wherein the bellows 33 is removably secured and disposed in the hollow interior 16 of the body portion 14 as shown.

Figure 5:
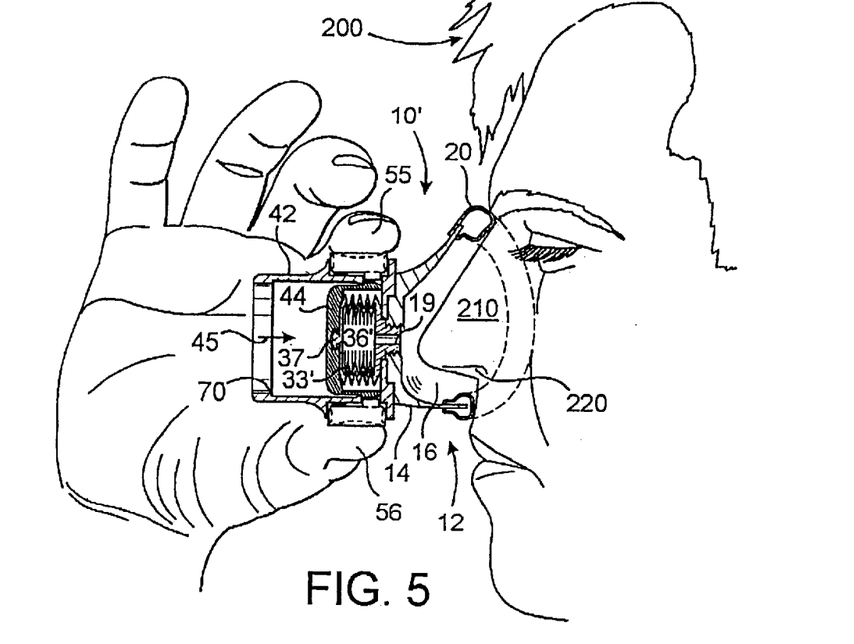
FIG. 5 is side view in partial section of yet another preferred embodiment of the present invention in an operative position on the face of the user.
Figure 6:
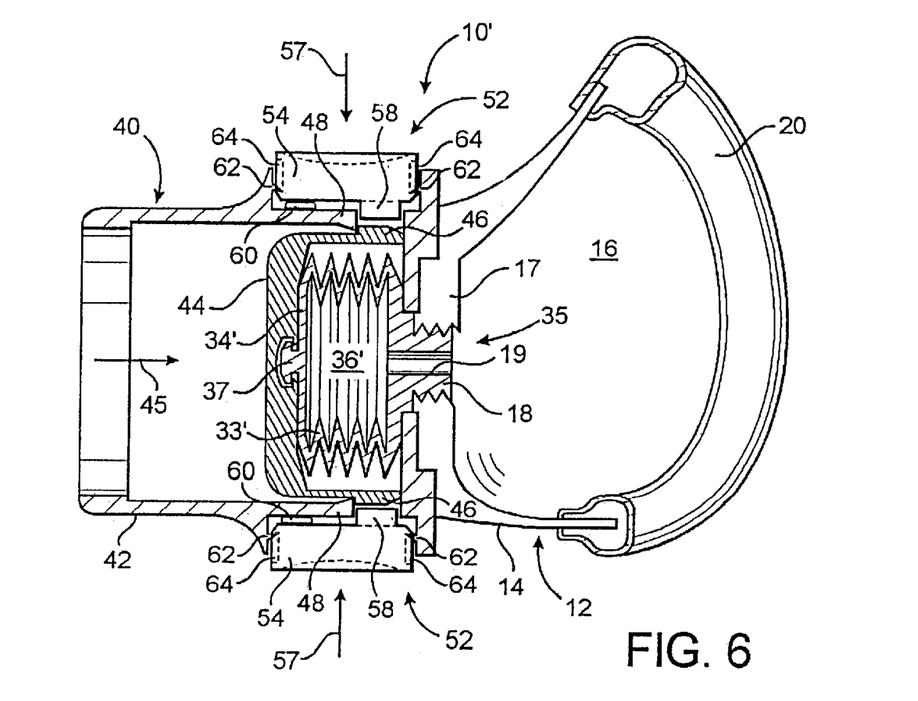
FIG. 6 is a detailed sectional view of the embodiment of FIG. 5.
Figure 7:
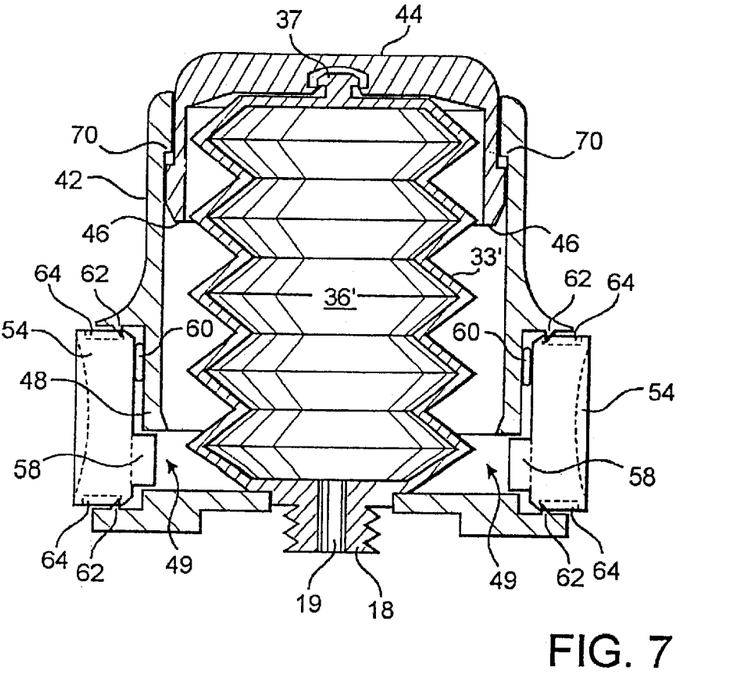
FIG. 7 is a detailed sectional view of certain structural components of the embodiment of FIGS. 5 and 6 where a pressure regulating assembly thereof is shown in an expanded position.

Looking to FIGS. 5, 6 and 7, the present invention comprises yet another preferred embodiment of the sinus pain relief assembly, generally indicated therein as 10'. This embodiment of the sinus pain relief assembly 10' is similar to that of the previously recited preferred embodiment sinus pain relief assembly 10 in that the pressure regulating assembly is primarily defined by an expandable bellows 33' formed of a plastic or like flexible material which is normally biased outwardly into the expanded position shown in FIG. 7. The vacuum chamber 36' is defined on the hollow interior of the bellows 33' and the bellows 33' is movable selectively from the expanded position of FIG. 7 to the collapsed position of FIG. 6 so as to remove the majority of air from the vacuum chamber 36'. Once so removed, the seal 20 is engaged in sealing relation and surrounding disposition about the nose 210 and an outwardly spaced relation to the nostrils 220 of the user 200.

Figure 6A:
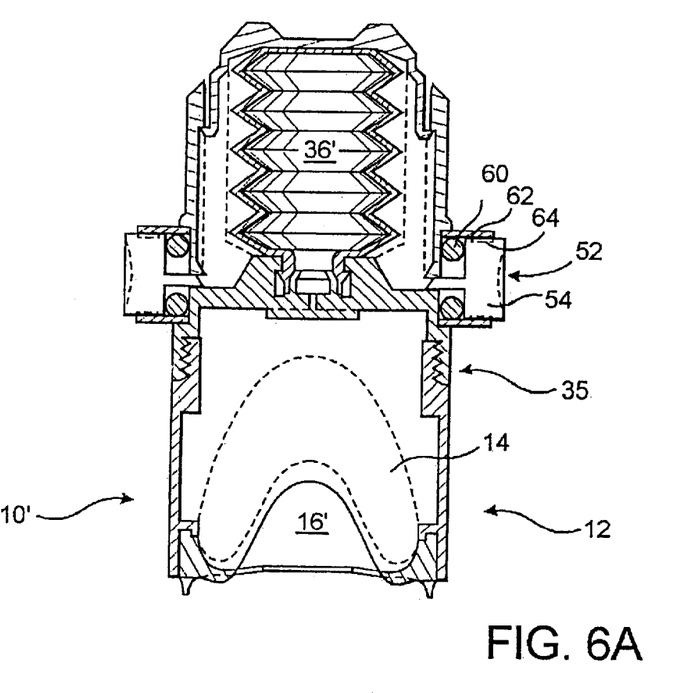
FIG. 6A is a detailed sectional view of a variation of the embodiment of FIG. 5 including external perimeter threading to achieve detachment of the mask.

Additional structural features of the preferred embodiment sinus pain relief assembly 10' include the existence of a housing generally indicated as 40 and including a somewhat sleeve like structure 42 disposed in surrounding, somewhat enclosing relation to the bellows 33' when it is either in its expanded position of FIG. 7 or its collapsed position of FIG. 6. Further, the sinus pain relief assembly 10' includes a positioning member 44 secured to the outer or distal end as at 34' of the bellows 33'. For example, although not necessary as in FIG. 6A, an integrally formed projection as at 37 of FIG. 5 may be used if desired. The positioning member 44 is connected to the bellows 33' so as to travel therewith and accomplish the selective positioning of the bellows 33' from its expanded position of FIG. 7 to its collapsed position of FIGS. 5 and 6. Such disposition is accomplished similarly to that of FIG. 10 in that a single finger of the user may be positioned on the exterior of the positioning member 44 and an inwardly directed force is applied thereto in accordance with directional arrow 45.

Also preferably included with the sinus pain relief assembly 10' of the present invention is a locking assembly. The locking assembly comprises one or more first locking components 46 integrally formed on the positioning member 44 and movable therewith. A second locking component comprises one or more inwardly directed shoulders as at 48 inwardly extending into the path of travel of the first locking components 46 of the positioning member 44. With reference to FIG. 6, inwardly directed force applied to the positioning member 44 will serve to position it until the second locking members 48 removably but lockingly engage the first locking component 46 on the positioning member as shown. It should be apparent that the bellows 33' is therefore retained within the collapsed position. The seal 20 is then applied in sealing engagement with the face and in surrounding relation to the nose 210 and nostrils 220 of the user 200. When properly sealed and when the hollow interior 16 of the body portion 14 and the vacuum chamber 36' are in direct fluid communication with one another a release mechanism generally indicated as 52 is activated. Such activation occurs by an inwardly directed force being exerted on release members 54 by appropriately positioned fingers 55 and 56 of the user 200. Such inwardly directed force in accordance with directional arrows 57 will cause fingers 58 attached to the members 54 to engage the first locking components 46 on the positioning member 44. This will cause an inward flexing of the first locking members 46 and a disengagement of these locking members 46 from the second locking members 48. The inherent flexibility and structural bias of the bellows 33' will thereby cause the bellows to move outwardly into the expanded position shown in FIG. 7. A negative pressure will be created in the nasal cavity 28 (See FIG. 1) as air flows therefrom through the hollow interior 16 of the body portion 14 and through passage 19 into the interior of the vacuum chamber 36'. Operation of the release assembly 52 is facilitated through the provision of biasing members as at 60 serving to normally position the release members 54 in there outermost position as shown in FIG. 6. Projections 62 preferably integrally formed on the housing body 42 slide within the tracks or grooves integrally formed in the release member 54 so as to properly orient and position the release member 54 for operation as described above.

With reference to FIG. 7, one or more block members as at 70 are integrally formed on the housing body 42 and limit the outermost extension of the positioning member 44 through engagement with the first locking components 46 as clearly disclosed.

Figure 8:
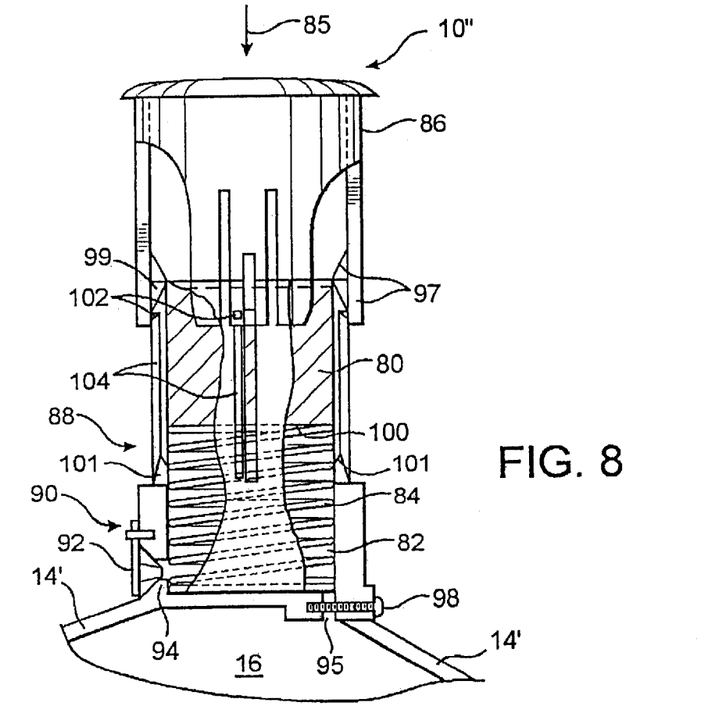
FIG. 8 is yet another preferred embodiment of the present invention.
Figure 9:
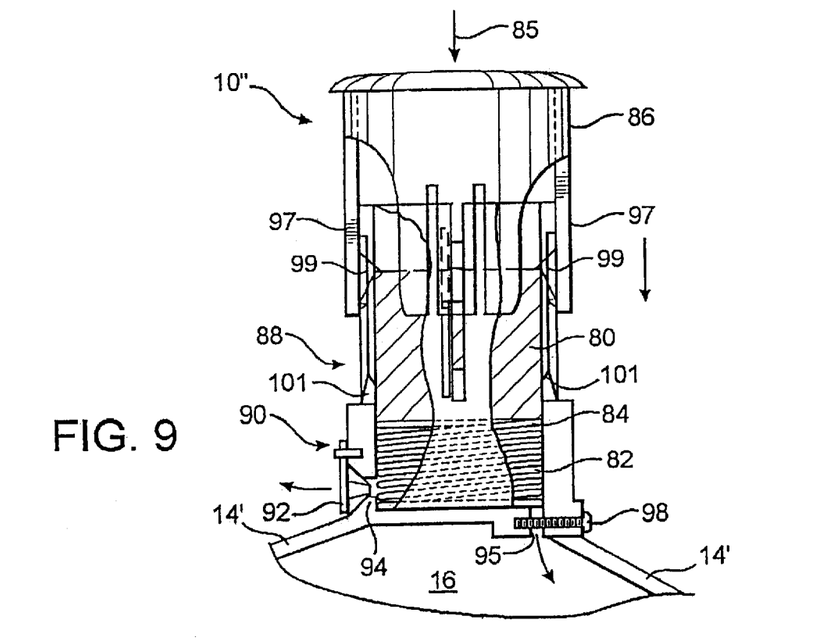
FIG. 9 is a sectional view in partial cutaway of the embodiment of FIG. 8 in a different operative position.

Yet another preferred embodiment of the sinus pain relief assembly 10" is shown in various operative positions in FIGS. 8–12. More specifically, the sinus pain relieving assembly 10" includes a movable vacuum piston 80 movably mounted within a vacuum chamber 82 and biased by a biasing spring 84 into its normally outer, expanded position, as shown in FIG. 8. The movement of the piston 80 is accomplished by manipulation of a positioning member 86 initially connected to an outermost end of the piston 80, as best shown in FIG. 8. The pressure regulating assembly includes a body 88 having a hollow interior which defines the vacuum chamber 82 and in which the piston 80 moves between the aforementioned expanded positions of FIG. 8 and the collapsed position of FIG. 11. A vent assembly 90 is formed on the housing 88 of the pressure regulating assembly and comprises a valve member 92 preferably in the form of a flap valve serving to normally seal a vent aperture 94. However, when the piston 80 is directed inwardly into the vacuum chamber 82 and into its collapsed position (See FIG. 11), air normally within the vacuum chamber 82 will be exhausted through vent aperture 94 as the flap valve 92 is forced outwardly to release air pressure therein. The positioning member 86 is of course manipulated by an appropriate finger of the hand of the user to apply the force as indicated by directional arrow 85. Similarly, a vacuum passage as at 95 serves to establish direct fluid communication between the vacuum chamber 82 and the hollow interior 16' of the body portion 14' as well as the interior of the nasal cavity 28 once the seal 20 (not shown) is in its aforementioned sealed engagement on the face of the user. An adjusting screw is disposed and structured to regulate the size of vacuum passage 95.

Other structural features of the additional embodiment of the sinus pain relief assembly 10" includes a lock and unlock components in the form of elongated arms as at 97 being formed of a flexible material and integrally attached to the positioning member 86. In addition, piston engagement tangs as at 99 are also integrally formed on the lock and unlocking arms 97 so as to travel therewith. In the position shown in FIG. 8 these tangs 99 engage the outermost end of the piston 80 and force it downwardly from the expanded position of FIG. 8 into the collapsed position of FIG. 11. Such tangs 99 travel in piston engaging tang slots 100 formed in the housing 88 of the pressure regulating assembly for guidance of the positioning member 85 during the reciprocal travel during its stroke. Further, an unlocking shoulder as at 101 is also included and integrally formed on the housing 88 and disposed in interruptive relation to the downward travel of the piston engaging tangs 99. Once the shoulders 101 engage the tangs 99 the lock and unlocking arms 97 will be forced outwardly (See FIG. 11) causing the release of the positioning member 86 from the piston and an upward travel of the positioning member as well as the beginning upward travel of the piston 80. Upward travel into its expanded position of the piston 80 will be caused by the force exerted thereon by the biasing spring 84.

Figures 10, 11, 12:
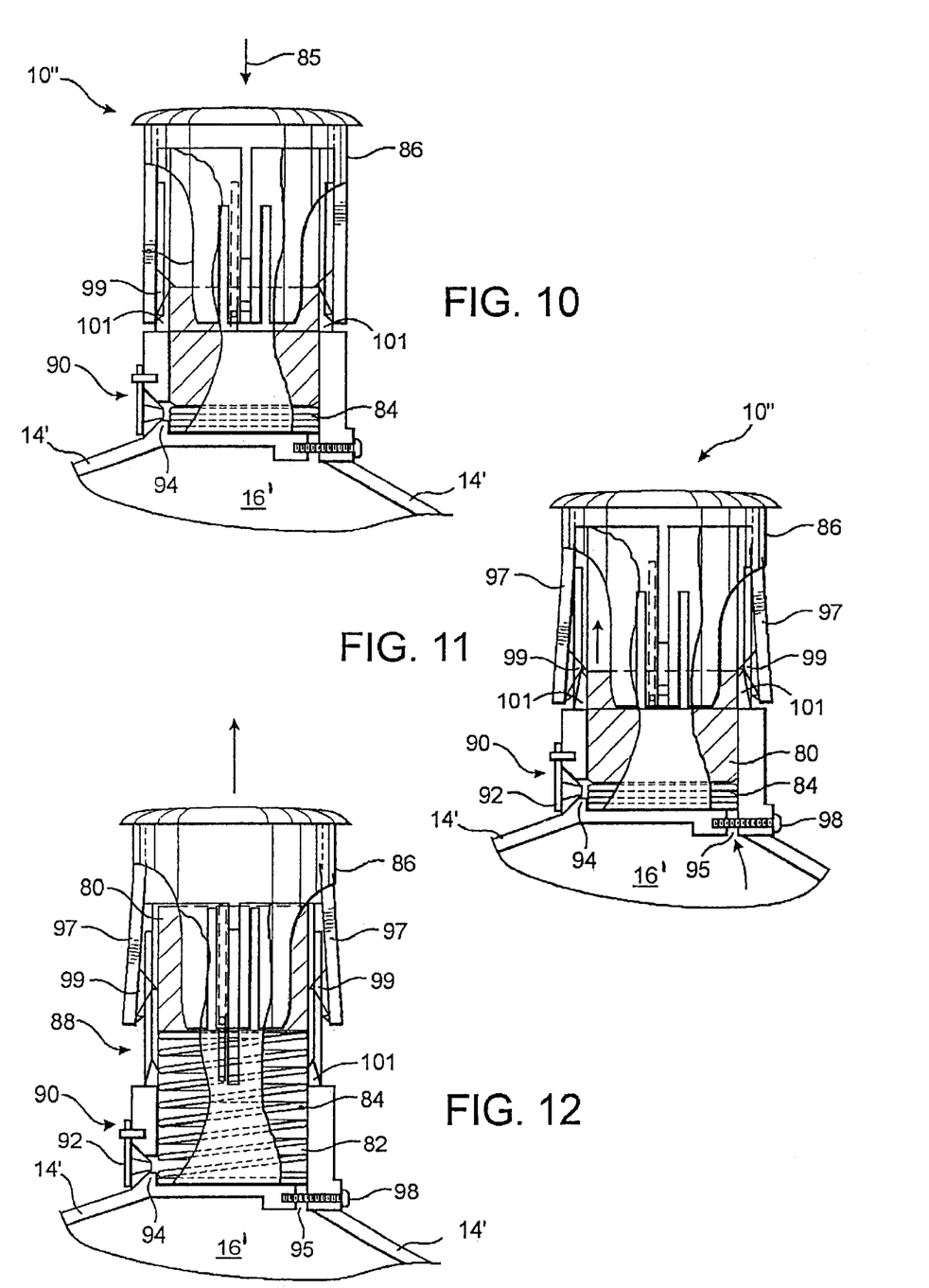
FIG. 10 is a sectional view in partial cutaway of the embodiment of FIGS. 8 and 9 in a different operative position.
FIG. 11 is a sectional view in partial cutaway of the embodiment of FIGS. 8, 9 and 10 in a different operative position.
FIG. 12 is a sectional view in partial cutaway of the embodiments of FIGS. 8–11 in a different operative position.

An up lock 102 formed on the positioning member 86 is structured and disposed to travel within up lock grooves 104 formed on the housing 88 and serve to limit the outer extension of the positioning member 86 as best shown in FIG. 8. A thorough review of the various operative positions shown in FIGS. 8–12 show that a downward force 85 exerted on the positioning member 86 will cause a downward travel of the piston 80 into its collapsed position as shown in FIG. 10. The continued downward travel of the positioning member 86 will in turn cause an engagement of the unlocking shoulders 101 with the tangs 99 of the locking and unlocking arms 97. The positioning member 86 will therefor be disengaged from the piston allowing the upward traveling of the piston 80 due to the force exerted thereon by the biasing spring 84 and the eventual upward travel of the positioning member 86.

Figure 13:
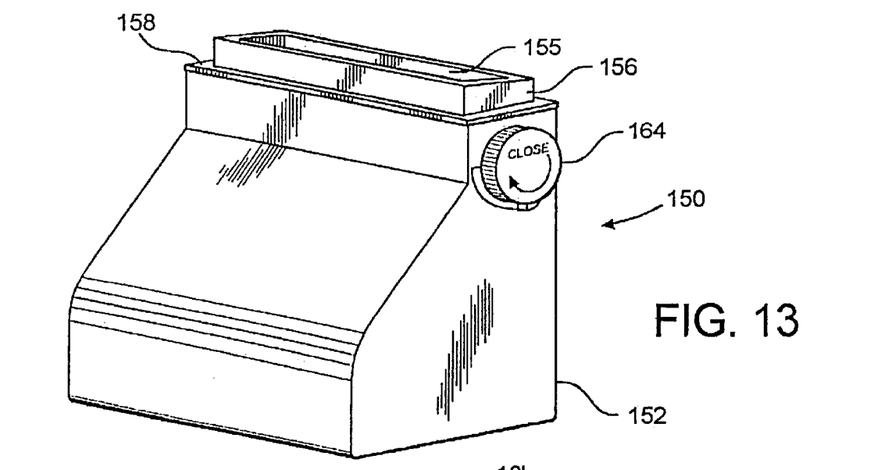
FIG. 13 is a perspective view of yet another preferred embodiment of the present invention relation to a hydrator assembly.
Figure 14:
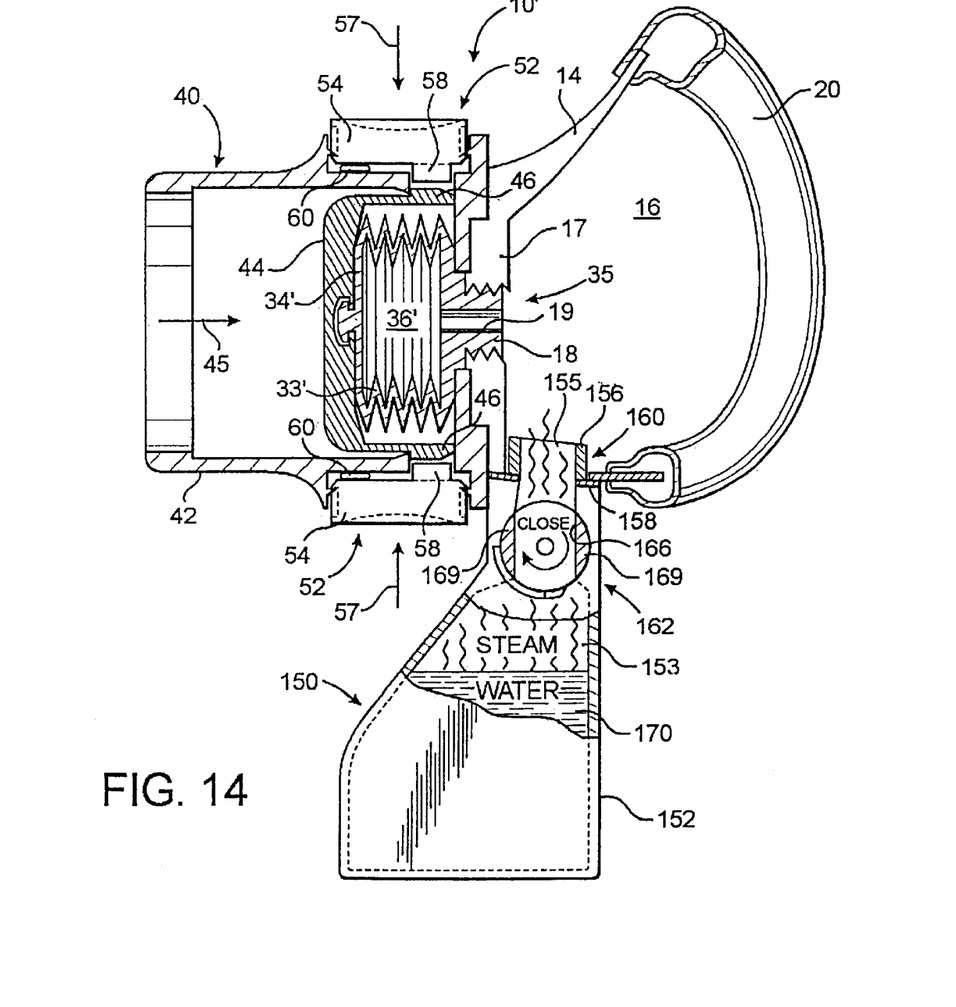
FIG. 14 is a sectional view in partial cutaway showing the hydrator assembly of FIG. 13 attached to the structural embodiment of FIG. 6.

Yet another preferred embodiment of the present invention is shown in FIGS. 13 and 14 wherein a hydrator assembly generally indicated as 150 includes a hydrator housing 152 having a hollow interior (See FIG. 14) 153. The upper end of the housing 152 has an opening as at 155 surrounded by a mating or connecting collar 156. A gasket or seal structure 158 is disposed in surrounding relation to the connecting collar 156 and is specifically adapted to engage an outer surface of the body portion 14' of the mask in order to establish sealing engagement therewith. The upper opening or aperture 155 communicates directly with the hollow interior 16 of the body portion 14' in that the connecting or mating collar 156 passes through a specifically dimensioned and configured opening as at 160 integrally formed in the body portion 14'. When the hydrator assembly 150 is not being used or is disposed in detached relation to the body portion 14', a plug or like closure element (not shown for purposes of clarity) may be used to close the opening 160 in the body portion 14'.

The hydrator assembly 150 of the present invention also preferably includes a valve assembly 162 including an externally accessible knob 164 which may be selectively positioned between an opened and a closed position by the hand of the user or patient. When in the open position, as shown in FIG. 14, the valve structure 162 includes an integrally, interiorly formed passage 166 which is disposed to establish fluid communication between the interior 153 of the hydrator body 152 and the opening 155 in the upper end thereof. This of course establishes direct fluid communication with the hollow interior 16 of the body portion 14' and also with the nasal cavity and nasopharynx once the body portion 14' is properly applied to and sealed about the nose and nostrils of the user as best shown in FIG. 5.

In operation, prior to fitting the hydrator body 152 to the body portion 14', it is filled with hot water or saline solution as at 170, while the valve structure 162 is in its opened position. Once filled, the valve structure is moved to its closed position such that solid portions as at 169 of the valve structure 162 serve to block communication between the interior 153 and the opening 155. With the valve in its closed position, the opening 155 is placed in direct communication with the hollow interior 16 of the body portion 14' by the insertion of the connecting collar 156 through the opening 160 and by establishing sealing engagement with the exterior of the body portion 14' due to the provision of the aforementioned gasket or seal structure 158. The pressure regulating assembly is then positioned into its collapsed position as shown in FIG. 14. Once in the collapsed position, the valve structure 162 is opened to the position shown in FIG. 14 and water vapor or steam is allowed to pass upwardly and into the hollow interior 16 of the body portion 14'. When adequate nasal cavity and/or nasopharynx pre-hydration has been achieved, the valve structure 162 is again disposed in its closed position. Following pre-hydration, the patient or user swallows and the bellows 33' is released to assume its expanded position and thereby create an initial negative pressure within the nasal cavity and nasopharynx.

Since many modifications, variations and changes in detail, such as the use of a small vacuum pump, can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described.

What is claimed is:

1. A non-invasive method for relieving sinus pain of a person, said method comprising:
   a) isolating the nasal cavity from external ambient pressure,
   b) isolating the nasal cavity from fluid communication with the esophagus,
   c) creating a predetermined negative pressure within the nasal cavity, and
   d) establishing the predetermined negative pressure to be at least sufficient to cause fluid transfer from the sinus cavity into the nasal cavity.

2. A method as recited in claim 1 wherein isolating the nasal cavity comprises enclosing the nose and nostrils of the person.

3. A method as recited in claim 2 wherein isolating the nasal cavity further comprises establishing a substantially fluid tight seal about the nose and nostrils.

4. A method as recited in claim 3 comprising establishing a substantially fluid tight seal continuously and in outwardly spaced, surrounding relation to the nose and nostrils of the person.

5. A method as recited in claim 2 comprising establishing fluid communication between the nasal cavity and an interior of an isolating enclosure which encloses the nose and nostrils of the person.

6. A method as recited in claim 5 comprising including a negative pressure within the interior of the isolating enclosure and communicating the negative pressure to the nasal cavity through the nostrils of the person.

7. A method as recited in claim 6 comprising isolating the nasal cavity from the esophagus by establishing sealing engagement of the uvula with the back of the nasopharynx.

8. A method as recited in claim 7 further comprising establishing sealing engagement of the uvula with the back of the nasopharynx by the person swallowing.

9. A method as recited in claim 5 further comprising hydrating the nasal cavity at least minimally prior to creating a negative pressure within the nasal cavity.

10. A method as recited in claim 9 further comprising transferring a vapor into the interior of the isolating enclosure subsequent to isolating the nasal cavity from external ambient pressure and establishing fluid communication between the interior of the isolating enclosure and the nasal cavity.

11. A method as recited in claim 10 comprising hydrating the nasal cavity through the nostrils of the person.

12. A method as recited in claim 11 comprising creating a predetermined negative pressure within the nasal cavity subsequent to hydration of the nasal cavity.

13. A method as recited in claim 12 comprising creating a negative pressure within the interior of the isolating enclosure and communicating the negative pressure to the nasal cavity through the nostrils of the person.

14. A method as recited in claim 1 further comprising hydrating the nasal cavity at least minimally prior to creating a negative pressure within the nasal cavity.

15. A method as recited in claim 14 comprising hydrating the nasal cavity through the nostrils of the person.

16. A method as recited in claim 15 comprising creating the predetermined negative pressure within the nasal cavity subsequent to hydration of the nasal cavity.

17. A method as recited in claim 1 comprising isolating the nasal cavity from the esophagus by establishing sealing engagement of the uvula with the back of the nasopharynx.

18. A method as recited in claim 17 further comprising establishing a sealing engagement of the uvula with the back of the nasopharynx by the person swallowing.

19. A non-invasive method for relieving sinus pain of a person, said method comprising:
   a) isolating the nasal cavity and nasopharynx from external ambient pressure and from fluid communication with the esophagus,
   b) creating at least a predetermined minimal negative pressure within the nasal cavity and nasopharynx subsequent to and during isolation of the nasal cavity and nasopharynx, and
   c) establishing the predetermined minimal negative pressure to be sufficient to force fluid transfer from at least one sinus cavity to the nasal cavity.

20. A method as recited in claim 19 comprising isolating the nasal cavity from the esophagus by establishing sealing engagement of the uvula with the back of the nasopharynx.

21. A method as recited in claim 20 further comprising establishing sealing engagement of the uvula with the back of the nasopharynx by the person swallowing.

22. A non-invasive method of relieving sinus pain of a person, said method comprising:
   a) segregating the nose and nostrils from external ambient conditions, b) isolating the nasal cavity and nasopharynx from external ambient pressure by creating a substantially fluid tight seal in surrounding relation to at least the nose and nostrils of the person, c) restricting fluid communication between the nasal cavity and nasopharynx by establishing a sealing engagement between the uvula and the back of the nasopharynx, d) selectively establishing fluid communication between the nasal cavity and nasopharynx and a source of negative pressure, and e) subjecting the nasal cavity and nasopharynx to a sufficient negative pressure to force fluid flow from the sinus cavities into the nasal cavity.

23. A method as recited in claim 22 comprising positioning an enclosure in covering relation to the nose and nostrils of the person and in surrounding, substantially sealing engagement with the person's face to segregate the nose and nostrils from ambient conditions including isolating the nasal cavity from ambient pressure.

24. A method as recited in claim 23 comprising restricting fluid communication of the nasal cavity and nasopharynx with the esophagus concurrently to isolating the nasal cavity and nasopharynx from external ambient pressure.

25. A method as recited in claim 24 comprising restricting fluid communication with the esophagus by establishing sealing engagement of the uvula with the back of the nasopharynx by the person swallowing.

26. A method as recited in claim 24 comprising establishing direct fluid communication between the source of negative pressure and the nasal cavity and nasopharynx while the nasal cavity and nasopharynx are isolated from both external ambient pressure and from fluid communication with the esophagus.

27. A method as recited in claim 26 further comprising releasing the enclosure from substantially sealing engagement with the person's face by establishing fluid communication between the nasal cavity and nasopharynx and the esophagus.

28. A assembly as recited in claim 27 further comprising establishing fluid communication between the nasal cavity and the nasopharynx by disengaging the uvula from sealing engagement with the back of the nasopharynx.

29. A method as recited in claim 28 comprising disengaging the uvula from engaging relation with the back of the nasopharynx by the person swallowing.

* * * * *